United States Patent [19]

Snow et al.

[11] Patent Number: 5,539,117

[45] Date of Patent: Jul. 23, 1996

[54] 2-ACETYL-6-CYANOPYRIDINES AND THEIR USE AS INTERMEDIATES IN THE SYNTHESIS OF OLIGO-2,6-PYRIDINES

[76] Inventors: Robert A. Snow, 118 Cratin La., West Chester, Pa. 19380; Daniel J. Delecki, 141 Upper Gulph Rd., Radnor, Pa. 19087; Chandra R. Shah, 333 Lancaster Ave., Apt. 500, Frazer, Pa. 19355; K. Robert Hollister, 8 Sycamore La., Chester Springs, Pa. 19425

[21] Appl. No.: 277,193

[22] Filed: Jul. 19, 1994

Related U.S. Application Data

[62] Division of Ser. No. 46,221, Apr. 13, 1993, Pat. No. 5,350,696.

[51] Int. Cl.$^6$ .................... C07D 213/84; C07D 213/22; C07F 7/02

[52] U.S. Cl. .................... 546/14; 546/257; 546/258; 546/287; 546/326

[58] Field of Search ..................... 546/14, 287

[56] References Cited

FOREIGN PATENT DOCUMENTS

WO90/00550  1/1990  WIPO ..................... 546/257

*Primary Examiner*—Alan L. Rotman
*Attorney, Agent, or Firm*—Dressler, Goldsmith, Shore & Milnamow, Ltd.

[57] ABSTRACT

The present invention is directed to 2-acetyl-6-cyanopyridine compounds that are useful as intermediates in the synthesis of oligo-2,6-pyridines. The present invention is also directed to new, simpler, less expensive methods for synthesizing such oligopyridines using the novel 2-acetyl-6-cyanopyridine compounds as intermediates.

3 Claims, No Drawings

2-ACETYL-6-CYANOPYRIDINES AND THEIR USE AS INTERMEDIATES IN THE SYNTHESIS OF OLIGO-2,6-PYRIDINES

This application is a division of application Ser. No. 08/046,221, filed Apr. 13, 1993, now U.S. Pat. No. 5,350,696.

FIELD OF THE INVENTION

The present invention relates to novel 2-acetyl-6-cyanopyridines and to their use as intermediates in novel syntheses of oligo-2,6-pyridines. The oligopyridines so produced are useful as complexing agents, which may, in turn, be incorporated in targeting immunoreagents which find particular utility in therapeutic and diagnostic imaging compositions and methods.

BACKGROUND OF THE INVENTION

The use of oligo-2,6-pyridines as complexing agents that can be incorporated in targeting immunoreagents is disclosed, for example, in WO 92/08494 (PCT/US91/08253).

As discussed in WO 92/08494, these complexing agents solve several problems in the prior art, particularly as regards therapeutic and diagnostic imaging uses of targeting radioactive immunoreagents.

One drawback regarding the oligo-2,6-pyridines is the difficulty and costliness of heretofore known methods for their synthesis. Thus, the synthetic methods disclosed in WO92/08494 involve several difficult, extremely low temperature n-butyllithium reactions which require extremely low and carefully controlled reaction temperatures (−78° C.). The low temperature reactions of n-butyllithium in chemical manufacturing often require special reactors and present problems associated with solubilities of various reactants. It would therefore be very desirable to have alternative synthetic methods for the oligo-2,6-pyridines that require fewer steps and less drastic reaction conditions.

SUMMARY OF THE INVENTION

The present invention is directed to 2-acetyl-6-cyanopyridine compounds that are useful as intermediates in the synthesis of oligo-2,6-pyridines. The present invention is also directed to new, simpler, less expensive methods for synthesizing such oligopyridines using the novel 2-acetyl-6-cyanopyridine compounds as intermediates.

The alternative synthetic methods of preparing terpyridines are more cost effective (requiring an 8-10 step reaction) and eliminate two low temperature reactions utilizing n-butyllithium. This invention describes the following novel compounds and novel alternative synthetic methods through which various diversified analogs of terpyridines can be successfully prepared:

More particularly, in accordance with the invention, there are provided novel 2-acetyl-6-cyanopyridines having the formula:

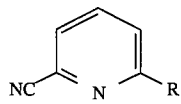

I wherein R is

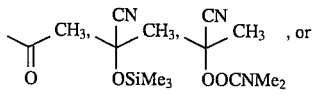

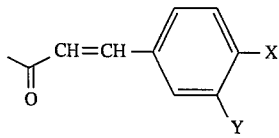

wherein X and Y are independently selected from the group consisting of H, OCH$_3$, and NO$_2$; or X and Y together form the group O—CH$_2$—O; and with the proviso that only one of X and Y is NO$_2$.

The use of these compounds in a synthetic method for preparing oligo-2,6-pyridine complexing agents which can be incorporated into targeting radioactive immunoreagents that are useful in therapeutic and diagnostic imaging compositions and methods is exemplified herein. This new improved synthetic process eliminates two low temperature (−78° C.) reaction steps, which are expensive and dangerous procedures. The new process further provides more synthetic diversities with fewer, shorter synthetic steps for preparing various oligo-2,6-pyridine complexing agents.

DETAILED DESCRIPTION OF THE INVENTION

The present invention is directed to novel 2-acetyl- 6-cyanopyridines having the formula:

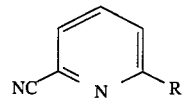

I wherein R is

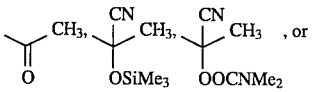

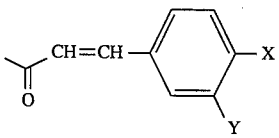

wherein X and Y are independently selected from the group consisting of H, OCH$_3$, and NO$_2$; or X and Y together form the group O—CH$_2$—O; and with the proviso that only one of X and Y is NO$_2$.

In a preferred embodiment, the novel 2-acetyl-6-cyanopyridines of the invention have the following structures:

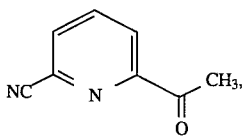

3a

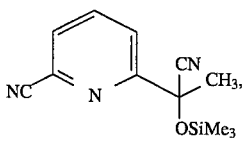

3b

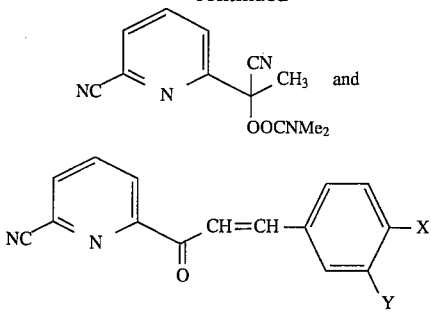

3c and

6

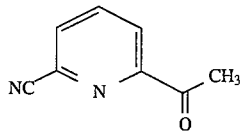

wherein X and Y are independently selected from the group consisting of H, OCH$_3$, and NO$_2$; or X and Y together form the group O—CH$_2$—O; and with the proviso that only one of X and Y is NO$_2$.

Most preferably, X is OCH$_3$, and Y is H.

These compounds are useful as intermediates in the synthesis of 4'-(3-amino-4-methoxyphenyl)-6,6"-bis[N,N-di-(carboxymethyl)aminomethyl]-2,2':6'2"-terpyridine (TMT), its monosodium, disodium, trisodium, and tetrasodium salts (each of which is referred to as the respective TMT sodium salt), and TMT-like analogues which are useful as chelating agents for therapeutic and diagnostic reagents.

The present invention is also directed to a method of synthesizing an oligo-2,6-pyridine which comprises (a) reacting a 2-acetyl-6-cyanopyridine of the formula:

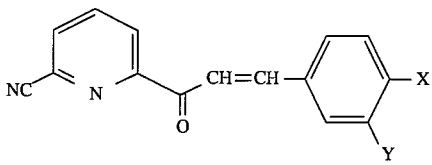

with pyridine and iodine for a time period and under conditions sufficient to form the corresponding pyridinium salt;

(b) reacting said 2-acetyl-6-cyanopyridine with a benzaldehyde for a time period and under conditions sufficient to form the corresponding 3-phenyl-2-propen-1-one; and (c) reacting said pyridinium salt from step (a) and said 3-phenyl-2-propen-1-one from step (b) for a time period and under conditions sufficient to form a dicyano-2,2':6',2"-terpyridine.

Preferred 3-phenyl-2-propen-1-one have the formula:

6 wherein X and Y are independently selected from the group consisting of H, OCH$_3$, and NO$_2$; or X and Y together form the group O—CH$_2$—O; and with the proviso that only one of X and Y is NO$_2$.

Most preferably, X is OCH$_3$, and Y is H.

Non-limiting examples of benzaldehydes include benzaldehyde and substituted benzaldehydes such as 4-methoxybenzaldehyde, 3-methoxybenzaldehyde, 3,4-dimethoxybenzaldehyde, 3,4-methylenedioxybenzaldehyde, 4-nitrobenzaldehyde, 3-nitrobenzaldehyde, 4-methoxy-3-nitrobenzaldehyde, and 3-methoxy-4-nitrobenzaldehyde. Preferably, the benzaldehyde is 4-methoxybenzaldehyde.

As is well known in the art, a reaction is carried out for a time period sufficient for the formation of the desired product. Reaction conditions suitable for the formation of the desired product depend upon, for example, time, temperature, solvent, additional necessary cofactors, reagents, catalysts and the like. Therefore, the time period and conditions under which a particular reaction is carried out depends upon the skill of the average worker in the art to determine the requisite parameters.

In a preferred embodiment, the pyridinium salt of this method is 1-[2-(6-cyano-2-pyridinyl)-2-oxoethyl]pyridinium iodide (sometimes herein referred to as 2-acetyl-6-cyanopyridine pyridinium iodide), and the 3-phenyl- 2-propen-1-one is 1-[2-(6-cyanopyridyl)]-3-( 4-methoxyphenyl)-2-propen-1-one. A preferred method of converting the 2-acetyl-6-cyanopyridine of this invention into a 3-phenyl-2-propen-1-one employs solid basic alumina as a catalyst which has the advantage of being readily separated from the reaction product by filtration.

In a further embodiment, this method comprises the further steps of (i) reducing said 6,6"-dicyano-2,2':6',2"-terpyridine for a time period and under conditions sufficient to form a 6,6"-bis(aminomethyl)-2,2':6',2"-terpyridine;

(ii) alkylating said 6,6"-bis(aminomethyl)-2,2':6',2"-terpyridine with an ester-containing alkylating agent for a time period and under conditions sufficient to form the corresponding tetraester; and (iii) saponifying said tetraester for a time period and under conditions sufficient to form a terpyridine chelating agent.

Reduction of the 6,6"-dicyano-2,2':6',2"-terpyridine is preferably accomplished by catalytic hydrogenation-which can be performed, for example, by the use of a palladium/carbon catalyst, as is well known in the art. A preferred solvent medium for reduction by catalytic hydrogenation is acetic acid. In the presence of a nitro group in a 4'-phenyl group attached to the 6,6"-dicyano-2,2':6',2"-terpyridine, a cyano group attached to a pyridine is preferably reduced by the action of sodium borohydride in the presence of diborane. A preferred solvent for this sodium borohydride/diborane reduction reaction is tetrahydrofuran (THF). Alkylation can be performed by the use of, for example, a carboxylic acid ester-containing alkylating agent such as, for example, methyl bromoacetate or ethyl bromoacetate, or phosphonic acid ester-containing alkylating agents such as, for example, diethyl chloromethylphosphonate. Preferably, the alkylating agent is a carboxylic acid ester-containing alkylating agent. Preferably, the carboxylic acid ester-containing alkylating agent is ethyl bromoacetate. Saponification can be performed with, for example, sodium hydroxide.

Preferably, the terpyridine tetraester formed in step (ii) above is the tetraethyl ester of 4'-(4-methoxyphenyl)- 6,6"-bis[N,N-di-(carboxymethyl)aminomethyl-]2,2':6'2"-terpyridine. This material is readily nitrated at the 3-position of the 4-methoxyphenyl group with nitric acid or potassium nitrate in sulfuric acid or in sulfuric acid and trifluoroacetic acid to form the tetraethyl ester of 4'-( 4-methoxy-3-nitrophenyl)-6,6"-bis[N,N-di-(carboxymethyl)aminomethyl]-2,2':6'2"-terpyridine, and the nitro group can be reduced, for example, by the action of ammonium formate in the presence of a palladium-on-carbon catalyst to form the tetraethyl ester of 4"-(3-amino-4-methoxyphenyl)-6,6"-bis[N,N-di-(carboxymethyl)aminomethyl]-2,2':6'2"-terpyridine. This material can then be treated as in step (iii) above.

Preferably, the terpyridine chelating agent formed by these additional reaction steps is 4'-(3-amino-4-methoxyphenyl)-6,6"-bis[N,N-di-(carboxymethyl)aminomethyl]-2,2':6'2"-terpyridine tetrasodium sodium salt. The chelating agent can also be a TMT analogue, as disclosed in WO 92/08494.

This 4'-(3-amino-4-methoxyphenyl)-6,6"-bis[N,N-di-(carboxymethyl)aminomethyl]-2,2':6'2"-terpyridine tetrasodium sodium salt can be acidified, for example, with hydrochloric acid, to produce 4'-(3-amino-4-methoxyphenyl)-6,6"-bis[N,N-di-(carboxymethyl)aminomethyl]-2,2':6'2"-terpyridine. Of cource, in an aqueous solution, as is well known, the tetrasodium salt can be in equilibrium with the trisodium salt which can be in equilibrium with the disodium salt which can be in equilibrium with the monosodium salt which can be in equilibrium with the tetraprotonic 4'-(3-amino-4-methoxyphenyl) 6,6"-bis[N,N-di-(carboxymethyl)aminomethyl]-2,2':6'2"-terpyridine. The relative concentrations of any of these materials is well recognized to be influenced by the pH of the medium which is influenced by additional buffer salts, temperature, added acid and added base.

In a further embodiment, this method comprises the further steps of (i) catalytically hydrogenating said 6,6"-dicyano-2,2':6",2"-terpyridine for a time period and under conditions sufficient to form a 6,6"-bis(aminomethyl)-2,2':6',2"-terpyridine; and (ii) directly alkylating said 6,6"-bis(aminomethyl)-2,2':6',2"-terpyridine for a time period and under conditions sufficient to form a terpyridine chelating agent.

Direct alkylation of said 6,6"-bis(aminomethyl)-2,2':6',2"-terpyridine can be performed with, for example, bromoacetic acid. The product of such an alkylation reaction between the 6,6"-bis(aminomethyl)-2,2':6',2"-terpyridine and bromoacetic acid is dependent on the ratio of reagents used in the reaction and can be a mono-, di-, tri-, or tetraalkylated 6,6"-bis(aminomethyl)-2,2':6',2"-terpyridine or a mixture containing one, two, three or four of these products, and components of which mixture can be separated from one another by means such as crystallization or chromatography, preferably reverse phase chromatography. Non-limiting examples of terpyridine chelating agents formed by these additional reaction steps include:

4'-(3-amino-4-methoxyphenyl)-6,6"-bis[N,N-di-(carboxymethyl)aminomethyl]-2,2':6'2"-terpyridine;

4'-(4-methoxyphenyl)-6,6"-bis[N,N-di-(carboxymethyl)aminomethyl]-2,2':6'2"-terpyridine;

4'-(4-amino-3-methoxyphenyl)-6,6"-bis[N,N-di-(carboxymethyl)-aminomethyl]- 2,2':6'2"-terpyridine;

4'-(3-methoxyphenyl)-6,6"-bis[N,N-di-(carboxymethyl)aminomethyl]-2,2':6'2"-terpyridine;

4'-(3,4-dimethoxyphenyl)-6,6"-bis[N,N-di-(carboxymethyl)aminomethyl]-2,2':6'2"-terpyridine;

4'-(3,4-methylenedioxyphenyl)-6,6"-bis[N,N-di-(carboxymethyl)aminomethyl]-2,2':6'2"-terpyridine;

4'-(4-methoxyphenyl)-6-aminomethyl-6"-carboxymethylaminomethyl- 2,2':6'2"-terpyridine;

4'-(4-methoxyphenyl)-6,6"-bis(carboxymethylaminomethyl)-2,2':6'2"-terpyridine;

4'-(4-methoxyphenyl)-6-aminomethyl-6"-[N,N-di-(carboxymethyl)aminomethyl]- 2,2':6'2"-terpyridine; and 4'-(4-methoxyphenyl)-6-carboxymethylaminomethyl-6"-[N,N-di-(carboxymethyl)aminomethyl]-2,2':6'2"-terpyridine.

In a preferred embodiment, the terpyridine chelating agent formed by these additional reaction steps is 4'-(3-amino-4-methoxyphenyl)-6,6"-bis[N,N-di-(carboxymethyl) aminomethyl]-2,2':6'2"-terpyridine as described above.

The 4'-(3-amino-4-methoxyphenyl)-6,6"-bis[N,N-di-(carboxymethyl)aminomethyl]-2,2':6'2"-terpyridine can be converted by the action of sodium hydroxide to the corresponding tetrasodium salt. The tetrasodium salt can be titrated to provide 4'-(3-amino-4-methoxyphenyl)-6,6"-bis[N,N-di-(carboxymethyl)aminomethyl]-2,2':6'2"-terpyridine by the action of a strong acid such as, for example, hydrochloric acid.

A key new intermediate in the formation of TMT, its sodium salts, and TMT-like analogues is 2-acetyl-6-cyanopyridine (Compound 3a). This compound is prepared according to Scheme 1, below, by treatment of pyridine-1-oxide (Compound 2) with cyanotrimethylsilane and dimethylcarbamyl chloride in dichloromethane. The reaction also yields four additional pyridine nitriles, including Compounds 3b and 3c, and which in turn can be used for the preparation of Compound 3a or other related disubstituted pyridines. Compound 3b can be converted to the cyanohydrin of Compound 3a, for example, by treatment with sodium hydroxide in the presence of water or with silver fluoride in the presence of water. Compound 3c can be converted to the cyanohydrin of Compound 3a, for example, by treatment with sodium hydroxide in methanol. The cyanohydrin of Compound 3a from Compound 3b or Compound 3c can be converted to Compound 3a by removal of the elements of HCN from the protected carbonyl group, for example, by treatment with sodium hydroxide or with basic alumina.

The 2,2':6',2"-terpyridine molecule (TMT and analogues) is widely used in transition metal chemistry as a coordinating, chelating ligand. The common synthetic approaches to terpyridines involve the coupling of two or three substituted pyridine units. Numerous methods for the synthesis of a wide variety of substituted pyridines have been described in the art, involving principally either modification of a preformed pyridine nucleus or pyridine ring formation from suitably substituted precursors. These methods are fairly lengthy and the reaction steps are often inconvenient and expensive.

The novel cyanopyridines of the present invention can be readily used in the synthesis of TMT and its analogues. The versatile intermediate Compound 3a yields both the corresponding pyridinium salt (Compound 4) by reacting with pyridine and iodine, as well as a number of 1-[2-(6-cyanopyridinyl]-3-phenyl-2-propen-1-ones (for example, Compounds 6a through 6f) by condensation with respective phenyl-substituted benzaldehyde. An important intermediate for the synthesis of complexing agents is the 6,6"-dicyano-2,2':6',2"-terpyridine (Compound 7a), which was prepared by the condensation reaction of Compound 4 and Compound 6a with ammonium acetate.

An analogous synthetic method was used for the preparation of the 6,6"-dibromo-2,2':6',2"-terpyridine (Compound 12a) by the reaction of the corresponding pyridinium salt (Compound 10) and the conjugated ketone (Compound 11a), as shown in Scheme 2. The 6,6"-dibromo-2,2':6',2"-terpyridine (Compound 12a) was converted into the 6,6"-dicyano-2,2':6',2"-terpyridine (Compound 7a) by reaction with sodium cyanide and cuprous cyanide. An intermediate, 2-acetyl-6-bromo-pyridine (Compound 9), was prepared by the reaction of 2,6-dibromopyridine with n-butyllithium followed by dimethylformamide.

As illustrated in Scheme 3, a precursor (Compound 14a) to a target chelating agent (Compound 16a) is prepared by catalytic hydrogenation of the 6,6"-dicyano-2,2':6',2"-terpyridine (Compound 7a) followed by the alkylation reaction of the 6,6"-bis(aminomethyl)-2,2':6',2"-terpyridine (Compound 13a) with ethyl bromoacetate. Saponification of the tetraester (Compound 14a) gave Compound 16a, which can also be prepared by direct alkylation of Compound 13a with bromoacetic acid followed by tritration with sodium hydroxide. Compound 16a is representative of a class of TMT-like analogues whose synthesis is facilitated by the cyanopyridines of the present invention.
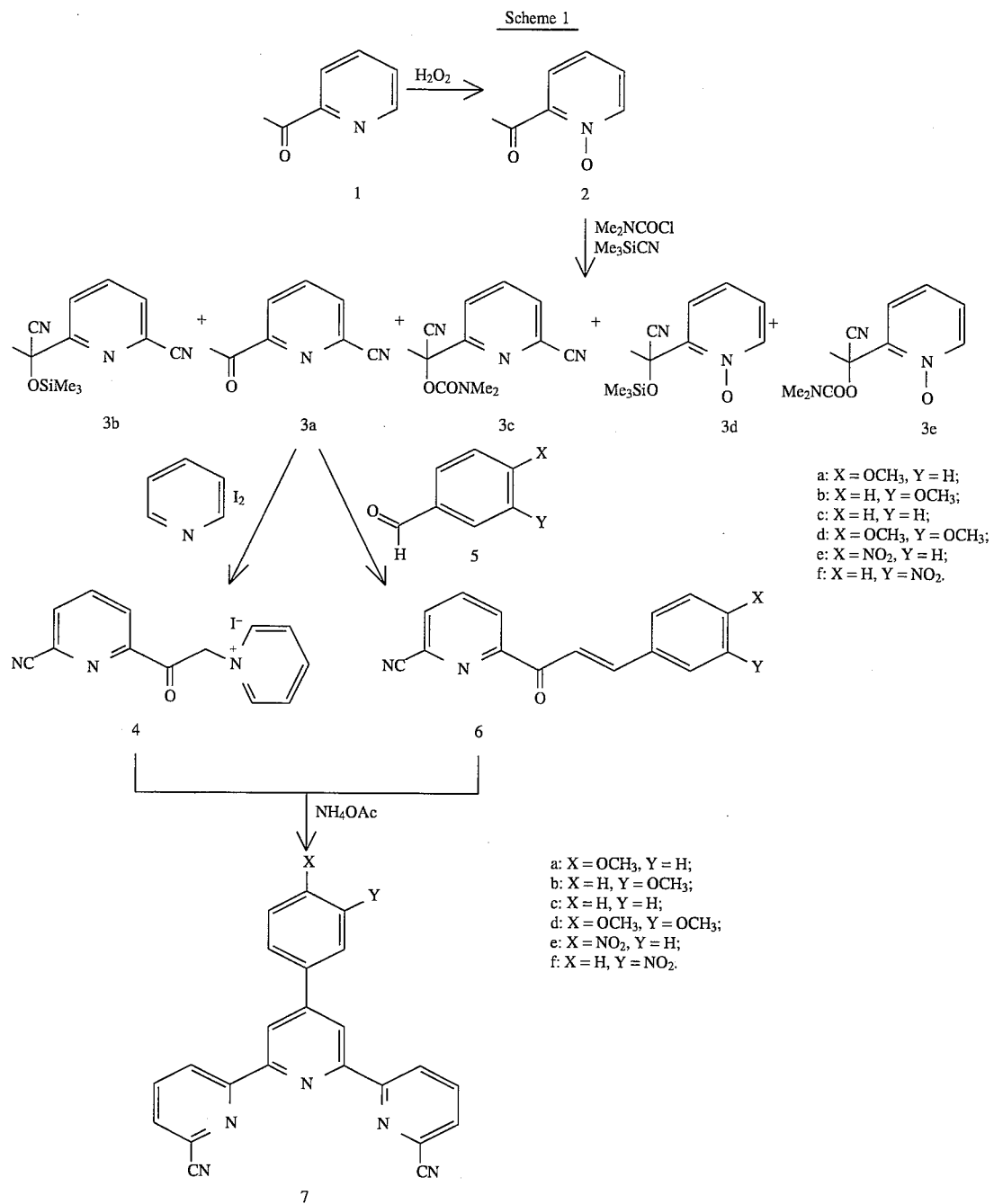

9
Scheme 2
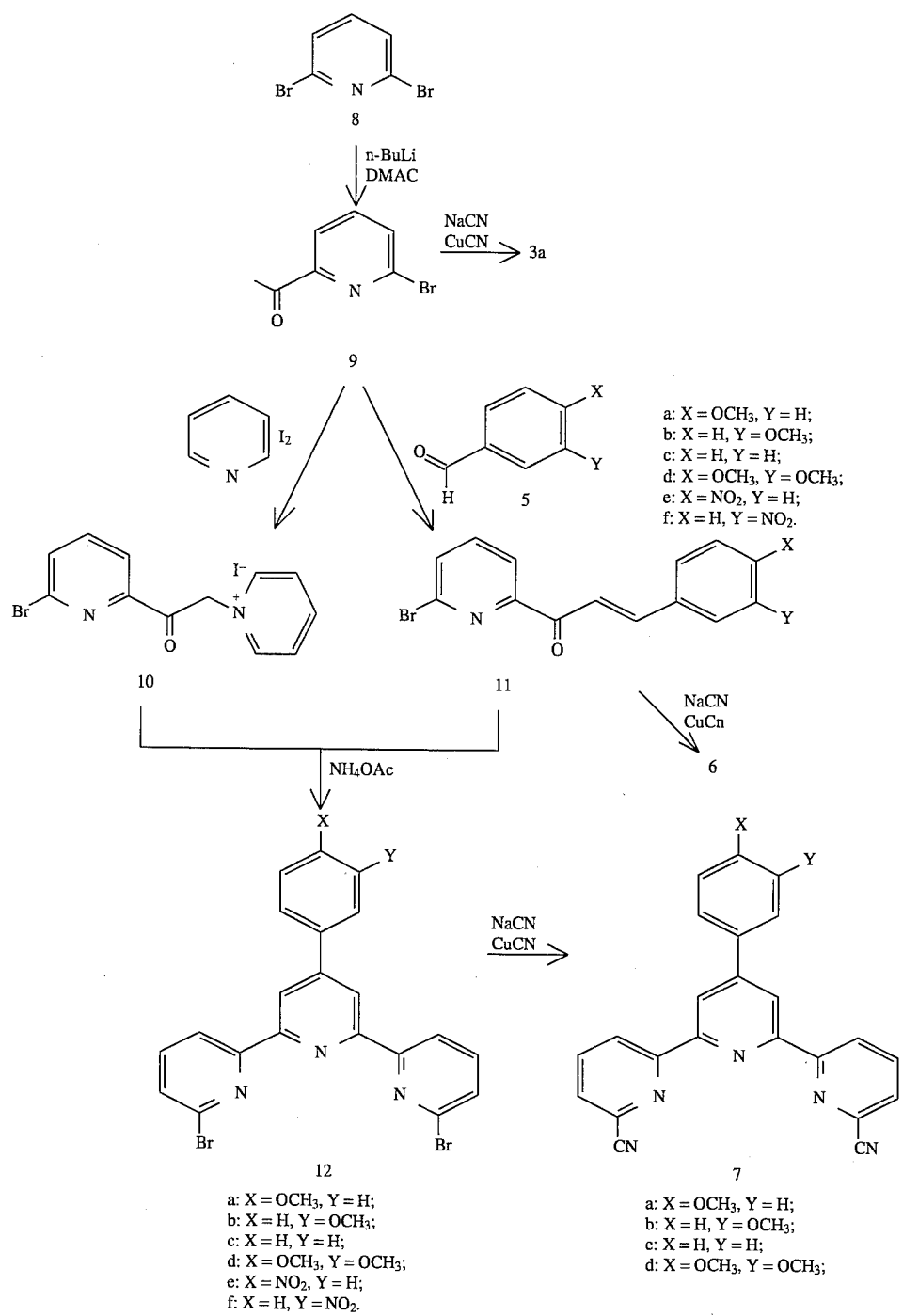

Scheme 3

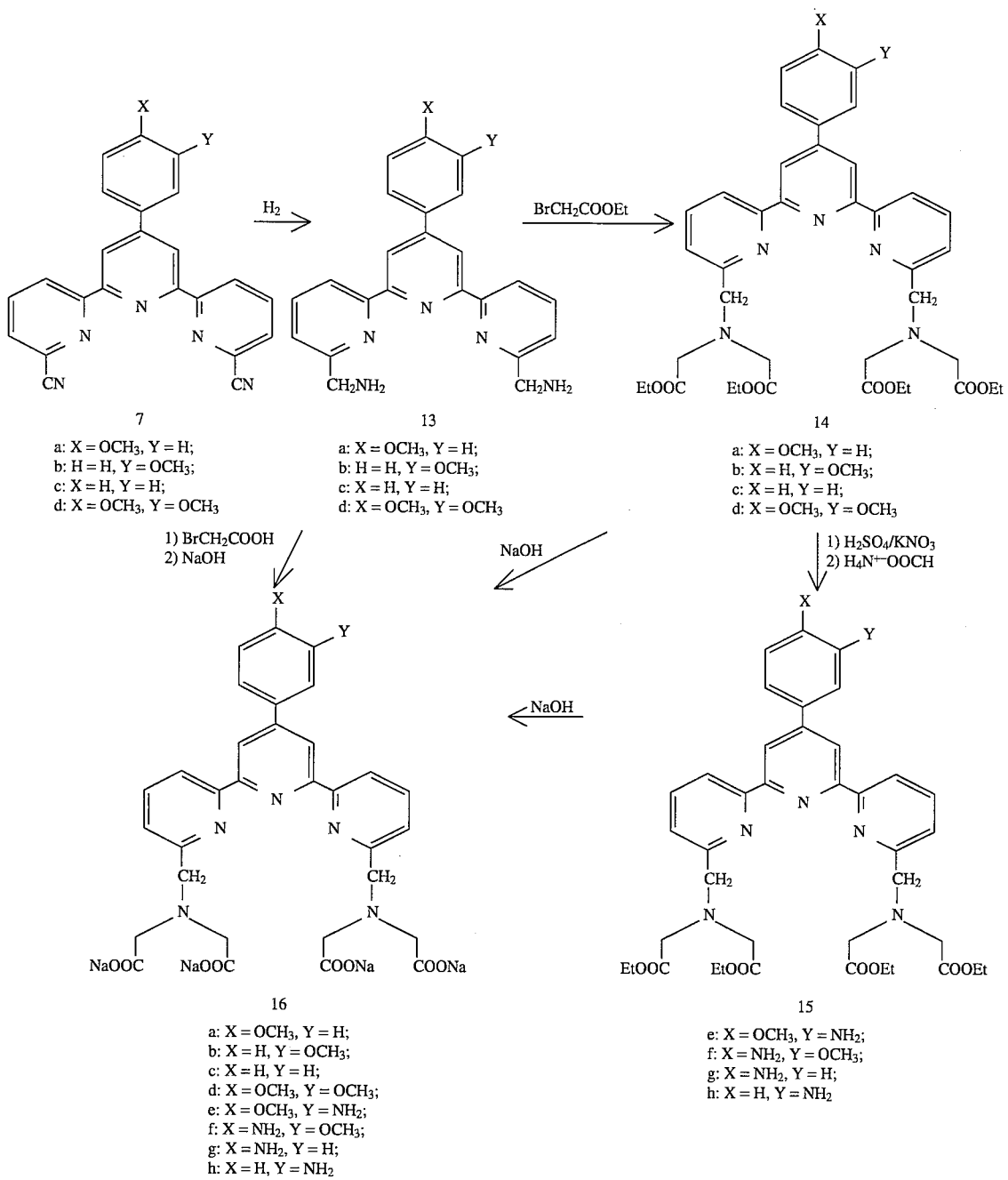

The following examples further illustrate the invention and are not to be construed as limiting of the specification and claims in any way.

EXAMPLE 1

2-Acetylpyridine-N-oxide (2)

To a solution of 2-acetylpyridine (0.3 mol) in 150 ml of glacial acetic acid was added with stirring 30% hydrogen peroxide (0.32 mol) and the mixture was allowed to react at 60°–65° C. for 16 hours. An additional 3.3 ml of 30% hydrogen peroxide was added, and the mixture was allowed to react at 70° C. for 2 hours. After cooling, the water was removed by evaporation at reduced pressure to leave a crude liquid residue which was taken up in an equal volume of 50:50 ethyl acetate and hexane, and the components were separated by chromatography on 330 g of silica gel. Gradient elution starting with 50:50 ethyl acetate/hexane to 100% ethyl acetate and then to 5% methanol gave 13.48 g (33% yield) of 2-acetyl-pyridine-N-oxide. $^1$H NMR (CDCl$_3$): 2.81 (singlet (s), 3H, CH$_3$), 7.34 (multiplet (m), 2H, H$_4$ and H$_5$), 7.71 (doublet (d), 1H, H$_3$), and 8.22 ppm (d, 1H, H$_5$); $^{13}$C NMR (CDCl$_3$): 31.3 (CH$_3$), 125.9, 127.4, 128.6, 141.2, and 195.7 ppm (C=O); mass spectrum (DCl) M$^+$H=138 m/e; IR (film) $\lambda_{max}$ 1686 cm$^{-1}$ (C=O).

EXAMPLE 2

2-Acetyl-6-cyanopyridine (3a, 3b, 3c, 3d, 3e)

To a solution of 2-acetylpyridine-N-oxide (0.098 mol) in 200 ml of methylene chloride was added dimethylcarbamyl chloride (0.1 mol) and the reaction mixture was allowed to react at room temperature under nitrogen for 24 hours. Additional dimethylcarbamyl chloride (0.1 mol) was added followed by cyanotrimethylsilane (0.22 mol), and the resulting mixture was allowed to react at 20° C. for 2 days. An additional 4 ml (0.03 mol) of cyanotrimethylsilane was then added, and the mixture was stirred at room temperature for another 24 hours. A solution of 200 ml of 10% $K_2CO_3$ was added to the reaction mixture and the resulting mixture was stirred for 45 minutes. The aqueous layer was extracted with 100 ml methylene chloride twice, the organic layers were combined and dried ($K_2CO_3$). After stripping the solvent, 16.9 g of crude product was isolated. The crude product obtained was chromatographed over Florisil® to isolate the desired products and the by-products with elution by the series of solvents: 2-acetyl-6-cyanopyridine (3a) (2g, 50% $CH_2Cl_2$/hexane), 2-cyano-6-(1-cyano-1-trimethysilyloxy-)ethylpyridine (3b) (0.81 g, $CH_2Cl_2$), 2-cyano- 6-(1-cyano-1-dimethylcarbamoyloxy)ethylpyridine (3c) (1.67 g, 25:72 EtOAc/$CH_2Cl_2$), 2-(1-cyano- 1-hydroxy)ethylpyridine (3d) (0.42 g, 50:50 EtOAc/$CH_2Cl_2$), and 2-(1-cyano-1-dimethylcarbamoyloxy)ethylpyridine-1-N-oxide (3e) (1.8 g, EtOAc). The products exhibited the following properties.

2-Acetyl-6-cyanopyridine (3a)

$^1$H NMR ($CDCl_3$): 2.75 (s, 3H, $CH_3$); 7.9 (d, 1H); 8.05 (triplet (t), 1H); and 8.25 ppm (d, 1H). $^{13}$C NMR ($CDCl_3$): 26.18 ($CH_3$); 117.23 (CN); 125:07; 131.89; 133.72; 138.84; 154.94 and 198.75 ppm (C=O).

MS (DCI) M+H=147 m/e.

IR ($CDCl_3$) $\lambda_{max}$ 1709 cm$^{-1}$, (C=O) [2244 cm$^{-1}$, weak, C=N].

2-Cyano-6-(1-cyano-1-trimethylsilyloxy)ethylpyridine (3b)

$^1$H NMR ($CDCl_3$): 0.3 (s, 9H, —SiMe$_3$); 1.96 (s, 3H, C—CH$_3$); 7.7 (d, 1H); 7.88 (d, 1H); and 7.95 ppm (two doublets, 1H). $^{13}$C NMR ($CDCl_3$): 1.7 (SiMe$_3$); 31.08 (C—CH$_3$); 72.66 (quaternary C); 117.2 (CN); 120.8 (CN); 123.2; 128.7; 133.6; 139.1 and 162.5 ppm.

MS (DCI) M+H=246 m/e.

Calculated for $C_{12}H_{15}N_3OSi$: C, 58.74%; H, 6.16%; N, 17.13%. Found C, 58.49%; H, 6.09%; N, 17.15%.

2-Cyano-6-(1-cyano-1-dimethylcarbamoyloxy)ethylpyridine (3c)

$^1$H NMR ($CDCl_3$): 2.05 (s, 3H, C-Me); 2.89 and 3.03 (two singlets, 3H and 3H, —N-M$_2$); 7.7 (m, 1H); and 7.94 ppm (m, 2H).

$^{13}$C NMR ($CDCl_3$): 28.37 (Me-C); 30.68 and 30.72 (Me-N); 73.9 (quaternary C); 116.2 (CN); 118.4 (CN); 124.4; 128.78; 131.9 weak (wk); 134.1 (wk); and 138.91 ppm.

IR(CDCl3) $\lambda_{max}$ 1720 cm (C=O) (2247 cm$^{-1}$, wk, CN).

2-(1-Cyano-1-trimethylsilyloxy)ethylpyridine-1-N-oxide (3d) $^1$H NMR ($CDCl_3$): 3.0 (s, 3H, Me); 7.3 (m, 2H); 7.6 (d, 1H); and 8.2 ppm (d, 1H).

13C NMR($CDCl_3$): 0.1 (SiMe3); 27 (Me-C—); 124; 126.2; 126.5; 141; and 119 ppm (wk, CN).

IR($CDCl_3$) no strong C=O absorption ($\lambda_{max}$~2250 cm$^{-1}$, wk, CN).

2-(1-Cyano-1-dimethylcarbamoyloxy)ethylpyridine-1-N-oxide (3e)

$^1$H NMR ($CDCl_3$): 1.64 (broad singlet (bs), 1H); 2.23 (s, 3H, C-Me); 2.95 and 3.08 (two singlets, 3H and 3H, Me$_2$N—); 7.3 (m, 2H); 7.45 (m, 1H); and 8.24 ppm (m, 1H).

$^{13}$C NMR ($CDCl_3$): 24.2 (Me-C—); 37.0 and 37.3 (Me$_2$N); 71.2 (quaternary C); 117.1 (CN); 124.0; 126.2; 126.4; and 141.3 ppm.

MS (DCI): M+H=226 (m/e).

IR ($CDCl_3$) $\lambda_{max}$ 1729 cm$^{-1}$ [—OC(=O)NMe$_2$] ($\lambda_{max}$ ~2250 cm$^{-1}$, wk, CN).

EXAMPLE 3

1-[2-(6-Cyano-2-pyridyl)-2-oxoethyl]pyridinium Iodide (4)

To a mixture of 2-acetyl-6-cyanopyridine (1.78 mmol) and iodine (1.78 mmol) was added 2.6 ml of pyridine and the resulting mixture was allowed to react at 100° C. under $N_2$ for 45 minutes. The reaction mixture was cooled, the product was isolated by filtration, washed with $CH_2Cl_2$, and dried under vacuum to yield 0.485 g of pyridinium salt (78%). $^1$H NMR (DMSO-D$_6$): 3.35 (s, exchanges with D$_2$O), 6.5 (s, 2H, —CH$_2$), 8.25 to 8.5 (m, 5H), 8.75 (t, 1H), and 8.97 ppm (~d, 2H); $^{13}$C NMR DMSO-D$_6$: 66.75 (—CH$_2$—), 117.1 (CN), 125.94, 128.19, 132.4 (weak), 133.95, 140.82, 146.71, 146.91, 151.92 (weak), and 190.30 ppm (C=O).

Molecular formula: $C_{13}H_{10}IN_3O$;

Calculated: C, 44.46; H, 2.87; N, 11.96; I, 36.14; Found: C, 44.45; H, 2.75; N, 11.84; I, 36.27.

EXAMPLE 4

1-[2-(6-cyanopyridyl)]-3-(4-methoxyphenyl)-2-propen-1-one (6a).

A mixture of 0.33 g of 2-acetyl-6-cyanopyridine, 0.28 mL of p-anisaldehyde, 1.9 g of basic alumina (activity grade I), and 6 mL of anhydrous tetrahydrofuran was stirred at room temperature under a nitrogen atmosphere for 24 hours. The reaction mixture was filtered, and the solid product was rinsed with fresh tetrahydrofuran (5 ml). The filtrate was evaporated under reduced pressure to yield a yellow solid residue which weighed 0.6 g. The product was purified using silica gel chromatography, eluting with 35% hexane in methylene chloride, to yield 0.4 g (72%) of desired material. A sample for combustion analysis was isolated by vacuum sublimation at 130° C. and 0.01 mm Hg. Melting point: 132.0° to 132.5° C. Mass spectrum: M+=264 m/e; IR (1% KBr): weak absorbance at $\lambda_{max}$=2237 cm$^{-1}$ (CN), strong absorbance at 1670 cm$^{-1}$ (unsaturated C=O), as well as 1591, 1566, 1512, 1257, 1217, 1181, and 1042 cm$^{-1}$; $^1$H NMR ($CDCl_3$): 4.87 (s, 3H, —OMe), 6.96 (d, 2H, 2 ortho H's on phenyl), 7.71 (d, 2H, 2 other ortho H's on phenyl), 7.85–8.15 (complex multiplet, 4H, pyridyl and vinyl), and 8.4 ppm (d, 1H); $^{13}$C NMR ($CDCl_3$): 14 lines corresponding to 14 distinct carbons: 56.0, 115.1, 117.4, 126.3, 128.2, 131.4, 131.5, 133.3, 138.8, 146.7, 156.0, 162.8, and 187.7 ppm.

Anal. Calc'd for $C_{16}H_{12}N_2O_2$: C, 72.71%; H, 4.58%; N, 10.60%. Found: C, 72.36%; H, 4.42%; N, 10.53%.

EXAMPLE 5

6,6"-Dicyano-4'-(4-methoxyphenyl)-2,2':6',2"-terpyridine (7a)

Vacuum dried 1-[2-(6-cyano-2-pyridyl)-2-oxoethyl]pyridinium iodide (192 mg, 0.55 mmol), 1-[2-(6-cyanopyridyl)]-3-(4-methoxyphenyl)-2-propen-1-one (145 mg, 0.55 mmol) and NH$_4$OAc (212 mg, 2.75 mmol) in 1.5 mL of acetic acid were heated to 80° C. for 1.5 hours, then for 6.5 hours at 65°

C., and then for 16 h at 90° C. Thin layer chromatography (silica gel; 70% hexane, 30% ether, 4% methanol, 1% triethylamine) indicated no starting 3-(4-methoxyphenyl)-1-[2-(6-cyanopyridyl)]-2-propenone remained. The reaction mixture was cooled in ice water; the desired precipitated product (196 mg) was isolated by filtration, and then triturated twice with water. Mass spectrum (FAB): M+H=390 m/e. $^1$H NMR (CDCl$_3$): 3.9 (s, 3H, OCH$_3$), 7.1 (d, 2H), 7.77 (d, 2H), 7.87 (d, 2H), 8.03 (t, 2H), 8.79 (s, 2H) and 8.85 ppm (d, 2H).

EXAMPLE 6

2-Acetyl-6-bromopyridine (9)

To a solution of 2,6-dibromopyridine (0.75 mol) in 2000 ml of anhydrous ether, which was cooled to −60° C. under N$_2$, was added a solution of n-butyllithium in hexane (0.75 mol) over 15 minutes. The reaction mixture was cooled to −80° C. and a solution of dimethylacetamide (0.86 mol) in 70 ml anhydrous ether was added slowly over 1 hour. After stirring the mixture for 15 minutes, a solution of NH$_4$Cl (0.93 mol) in 150 ml of water was added slowly over 8 minutes. After stirring an additional 45 minutes at room temperature, the aqueous layer was separated and extracted with 500 ml of ether. The combined organic layer was washed with water (2×800 ml), dried (MgSO$_4$), filtered, and stripped on a rotary evaporator to yield 159 g of the desired product. This material was distilled at 80° C./0.1 mm Hg to give a near colorless oil that crystallized readily on cooling.

EXAMPLE 7

1-[2-(6-Bromo-2-pyridinyl)-2-oxoethyl]-pyridinium iodide (10)

A mixture of 2-acetyl-6-bromopyridine (0.075 mol), 25 ml of pyridine, and iodine (0.075 mol) was allowed to react at 100° C. for 45 minutes and then cooled to room temperature. The reaction mixture was filtered, the solid product was triturated with CH$_2$Cl$_2$ (200 ml), isolated by filtration, and the residual solvent was removed under vacuum to yield 25.5 g (85%) of the desired salt. Melting point: 176°–178°C.

EXAMPLE 8

1-[2-(6-Bromopyridyl)]-3-(4-methoxyphenyl)-2-propen-1-one (11a)

To a stirred solution of 2-acetyl-6-bromopyridine (50 g; 0.25 mole) in 450 mL methanol was added 4-anisaldehyde (48 g; 0.35 mole). The mixture was cooled in a water bath to 20° C. and then a solution of KOH (18 g; 0.28 mole) in 100 mL H$_2$O was added rapidly. The light yellow mixture was stirred for 30 minutes and filtered. The cake was rinsed twice with isopropanol, and, after drying, gave 68 g (86% yield). Melting point: 106.1°–106.5° C. Mass spectrum (FDMS): 317 M+ (m/e).

Anal. for C$_{15}$H$_{12}$BrNO$_2$: Calcd: C, 56.63; H, 3.80; N, 4.40. Found: C, 56.66; H, 3.87; N, 4.41.

EXAMPLE 9

6,6"-Dibromo-4'-(4-methoxyphenyl)-2,2':6',2"-terpyridine (12a)

A mixture of 1-[2-(6-bromopyridyl)]-3-(4-methoxyphenyl)-2-propen-1-one (64 g; 0.20 mole), 1-[2-(6-bromo-2-pyridinyl)-2-oxoethyl]-pyridinium iodide (81 g; 0.20 mole) and ammonium acetate (77 g; 1.0 mole) in acetic acid (600 mL) was heated at 95° C. for 3 hours and then overnight at 60° C. The reaction mixture was cooled to 15° C. and the crystalline cake was filtered and rinsed with H$_2$O three times. After drying overnight 76.5 g (83%) of the desired product was obtained. Melting point: 205° C. Mass spectrum (FDMS): M$^+$=495 (m/e).

Anal. Calc'd for C$_{22}$H$_{15}$Br$_2$N$_3$O: C, 53,1; H, 3.0; N, 8.5. Found: C, 52.9; H, 3.1; N, 8.4.

EXAMPLE 10

6,6"-Dicyano-4'-(4-methoxyphenyl)-2,2':6',2"-terpyridine (7a)

A mixture of 6,6"-dibromo-4'-(4-methoxyphenyl)-2,2':6',2"-terpyridine (12a; 0.0745 mol), cuprous cyanide (0.296 mol), sodium cyanide (0.297 mol), and 300 ml of dimethylformamide was allowed to react at 160° C. for 6 hours. The solvent was evaporated under reduced pressure at 70° C., and the residual reaction mixture was transferred into 1500 ml of water containing 200 g of sodium cyanide. This mixture was stirred for 2 hours, the desired solid product was isolated by filtration, triturated with water (6×600 ml), isolated by filtration, and dried under vacuum for 16 hours at 50°–55° C. to yield 28.2 g (97% yield) of white powder which was recrystallized from methylene chloride (1 g per 90 mL). TLC: (silica gel plate; ethyl acetate:hexane::1:1 v/v) showed a single spot (Rf=0.5 approx.). Infrared spectrum: nitrile band around 2200 cm$^{-1}$; mass spectrum (FAB): M+H=390 m/e; $^1$H NMR (CDCl$_3$): 3.9 (s, 3H, OCH$_3$), 7.1 (d, 2H), 7.77 (d, 2H), 7.87 (d, 2H), 8.03 (t, 2H), 8.79 (s, 2H) and 8.85 ppm (d, 2H).

Analysis calculated for C$_{24}$H$_{15}$N$_5$O.1.75 H$_2$O: Calc'd: C, 68.50; H, 4.42; N, 16.60. Found: C, 68.51; H, 4.50; N, 16.20.

EXAMPLE 11

6,6"-Bis(aminomethyl)-4'-(4-methoxyphenyl)-2,2':6',2"-terpyridine (13a)

A mixture of 6,6"-dicyano-4'-(4-methoxyphenyl)-2,2':6',2"-terpyridine (7a; 4 mmol) and 480 mg of 10% Pd/C in 130 ml of acetic acid was hydrogenated (H$_2$, 50 psi) at 45° C. for 22 hours. The reaction mixture was filtered and the solvent was stripped to yield the desired diamine as the acetic acid salt. After trituration with methanol followed by removal of solvent and drying, 2 g (96% yield) of 6,6"-bis(aminomethyl)- 4'-(4-methoxyphenyl)-2,2':6',2"-terpyridine as the acetic acid salt was isolated. $^1$H NMR (DMSO-D$_6$): 3.85 (s, 3H, OCH$_3$), 4.07 (s, 4H, CH$_2$—N), 7.16 (d, 2H), 7.55 (d, 2H), 7.99 (d, 2H), 8.03 (t, 2H), 8.52 (d, 2H) and 8.78 ppm (s, 2H).

EXAMPLE 12

6,6"-Bis[N,N-di-(carboxymethyl)aminomethyl]-4'-(4-methoxyphenyl)-2,2':6'2"-terpyridine tetraethyl ester (14a)

A mixture of 6,6"-bis(aminomethyl)-4'-( 4'-methoxyphenyl)-2,2':6',2"-terpyridine (13a; 1.13 mmol), ethyl bromoacetate (4.65 mmol), and K$_2$CO$_3$ (1.2 mmol) in dimethylformamide was allowed to react at 85° C. for 60 hours. After an addition of K$_2$CO$_3$ (4.65 mmol), the reaction mixture was allowed to react at 85° C. for 20 hours. The reaction mixture was filtered and DMF was distilled under diminished pressure to yield 1 g of crude amino ester. The crude product was triturated with water, extracted with ethyl acetate, and dried. Upon distillation of ethyl acetate, 0.89 g of the desired amino-ester was isolated.

EXAMPLE 13

4'-(4-Methoxyphenyl)-2,2':6'2"-terpyridine-6,6"-dicarboxaldehyde

A solution of dibromide (7.46 g, 15.1 mmol) in 100 mL of dry THF was added dropwise to a solution of n-butyllithium (45 mmol) in 20 mL of tetrahydrofuran (THF) at −78° C. under $N_2$ over 12 minutes. After 10 minutes the reaction mixture was treated with dimethylformamide (7.5 mL) in THF (15 mL), and then quenched after 15 minutes with aqueous 10% HCl. The product was extracted into cold chloroform which was washed with saturated sodium chloride solution, filtered, and the solvent was evaporated. The solid residue was triturated with $CH_3CN$, filtered, and recrystallized from ethyl acetate to yield 3.53 g (60%); Melting point: 228°–229° C. FDMS (m/e) 395M.

Anal. Calcd for $C_{24}H_{17}N_3O_3$: C, 72.90; H, 4.33; N, 10.63. Found: C, 72.44; H, 4.31; N, 10.46.

EXAMPLE 14

6,6"-Bis(hydroxymethyl)-4'-(4-methoxyphenyl)-2,2':6',2"-terpyridine

A suspension of 4'-(4-methoxyphenyl)-2,2':6'2"-terpyridine-6,6"-dicarboxaldehyde (3.53 g, 8.93 mmol) in a mixture of 70 mL of THF and 70 mL of absolute EtOH was treated with 1 g of $NaBH_4$ and then heated to reflux for 15 minutes under $N_2$. After cooling, the organic solvents were removed, the residue was heated for 30 minutes at reflux in dilute $NaHCO_3$, cooled, filtered, washed with $H_2O$, then dried to give the desired product as a white solid (3.35 g, 94.4%). Melting point: 187°–189° C. FDMS (m/e) 400 $MH^+$, 399M.

Anal. Calcd for $C_{24}H_{21}N_3O_3$: C, 72.17; H, 5.30; N, 10.52. Found: C, 71.71; H, 5.20; N, 10.37.

EXAMPLE 15

6,6"-Bis(hydroxymethyl)-4'-(4-methoxyphenyl)-2,2':6',2"-terpyridine dimethanesulfonate To a suspension of 6,6"-bis(hydroxymethyl)-4'-(4-methoxyphenyl)- 2,2':6',2"-terpyridine (15.4 g, 38,5 mmol) in $CH_2Cl_2$ (175 mL) and $Et_3N$ (17 mL; 120 mmoles) at 8° C. a solution of$(CH_3SO_2)_2O$ (16.8 g, 96.5 mmol) in 50 mL of $CH_2Cl_2$ over 10–15 minutes. The reaction mixture was then extracted with water (200 mL), dried over $Mg_2SO_4$, filtered, and concentrated nearly to dryness. Addition of EtOAc produced the bismesylate as white crystals which were collected and dried (17.2 g, 80.4%). Melting point: 190°–192° C.

EXAMPLE 16

6,6"-Bis[N,N-di-(carboxymethyl)aminomethyl]-4'-(4-methoxyphenyl)-2,2':6'2"-terpyridine tetraethyl ester (14a)

A mixture of 6,6"-bis(hydroxymethyl)-4'-(4-methoxyphenyl)- 2,2':6',2"-terpyridine dimethanesulfonate (0.50 g, 0.96 mmol), di-isopropylethylamine (0.26 g, 2.0 mmol), and diethyl iminodiacetate (0.38 g, 2.0 mmol) was stirred for 16 hours in 20 mL of dry DMF. The solvent was evaporated under vacuum, and the residue was partitioned between equal volumes of ether and water. The ether was washed twice with water, dried over $Na_2SO_4$ and evaporated to give the desired product (0.58 g, 82%).

Analysis calculated or $C_{40}H_{47}N_5O_9$; Calculated: C, 64.76; H, 6.39; N, 9.44. Found: C, 64.35; H, 6.17; N, 9.39.

EXAMPLE 17

6,6"-Bis[N,N-di-(carboxymethyl)aminomethyl]-4'-(4-methoxy-3-nitrophenyl)-2,2':6'2"-terpyridine tetraethyl ester A solution of 6,6"-bis[N,N-di-(carboxymethyl)aminomethyl]- 4'-(4-methoxyphenyl)-2,2':6'2"-terpyridine tetraethyl ester (3.1 g; 40.6 mmoles) in trifluoroacetic acid (160 mL) at 15° C. was treated with potassium nitrate (4.4 g; 44 mmoles) followed by concentrated $H_2SO_4$ (22 g; 230 mmoles) added dropwise over 15 minutes. After 30 minutes the trifluoroacetic acid was recovered by distillation under reduced pressure, the residue was cooled, poured onto crushed ice, and treated with aqueous 10% $K_2CO_3$ until pH 8 was reached. The aqueous solution was extracted three times with ethyl acetate, the combined organic layers were washed with $H_2O$, saturated sodium chloride solution, dried over $Na_2SO_4$, filtered, concentrated to near dryness, and then dissolved in 90 mL hot absolute ethanol. On cooling, crystals were collected by filtration and rinsed with ethanol, and dried under vacuum to give 29 g (90%) of the desired product. Melting point: 81°–82° C. Mass spectrum (FDMS) (m/e) 787 $MH^+$, 786M.

Analysis calculated for $C_{40}H_{46}N_6O_{11}$; Calculated: C, 61.06; H, 5.89; N, 10.68. Found: C, 60.69; H, 6.22; N, 11.04.

EXAMPLE 18

6,6"-Bis[N,N-di-(carboxymethyl)aminomethyl]-4'-(3-amino-4-methoxyphenyl)-2,2':6'2"-terpyridine tetraethyl ester A mixture of 6,6"-bis[N,N-di-(carboxymethyl)aminomethyl]-4'-(4-methoxy-3-nitrophenyl)-2,2':6'2"-terpyridine tetraethyl ester (28.3 g; 36 mmoles) and 10% Pd/C (10 g; 10 mmoles) in THF (350 mL) and absolute ethanol (350 mL) under argon was treated with a solution of ammonium formate (9.4 g; 149 mmoles) in water (60 ml) over five minutes. The reaction mixture was stirred for 3 hours at reflux, cooled to 20° C., filtered, the catalyst was washed with 400 mL of absolute ethanol, and the filtrate was evaporated to dryness under vacuum to give 25.3 g (95%) of crude product which was further purified on silica gel with 10% $MeOH/CHCl_3$. FDMS (m/e) 757 $MH^+$, 756M.

Analysis calculated for $C_{40}H_{48}N_6O_9 \cdot \frac{1}{2}H_2O$; Calculated: C, 62.73; H, 6.45; N, 10.97. Found: C, 62.98; H, 6.47; N, 10.67.

EXAMPLE 19

6,6"-Bis[N,N-di-(carboxymethyl)aminomethyl]-4'-(3-amino-4-methoxyphenyl)-2,2':6'2"-terpyridine, tetrasodium salt.

A mixture of 6,6"-bis[N,N-di-(carboxymethyl)aminomethyl]-4'-(3-amino-4-methoxyphenyl)-2,2':6'2"-terpyridine tetraethyl ester (0.75 g, 0.99 mmol), sodium hydroxide (4 mmol), MeOH (50 mL), and triply distilled water (2 mL) was stirred for 16 hours at room temperature. Most of the solvent was removed under vacuum, the solid was isolated by filtration, rinsed twice with cold ethanol and once with hexane to give 0.72 g of the desired product (94%). Melting point: >290° C. Mass spectrum (FABMS) m/e 640 (M⁺ for tetracarboxylate).

Analysis calculated for $C_{32}H_{28}N_6O_9 \cdot 4Na \cdot 2H_2O$; Calculated: C, 50.01; H, 4.20; N, 10.93. Found: C, 49.82; H, 4.12; N, 10.74.

The invention has been described in detail with particular reference to certain preferred embodiments thereof, but it will be understood that variations and modifications can be effected within the spirit and scope of the invention.

What is claimed is:

1. A compound having a structure shown in the formula:

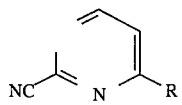

wherein —R is

or

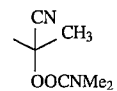

2. The compound of claim 1 having the structure:

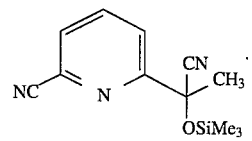

3. The compound of claim 1 having the structure:

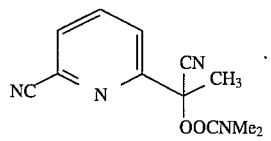

* * * * *